(12) United States Patent
Kocen et al.

(10) Patent No.: US 11,905,269 B1
(45) Date of Patent: Feb. 20, 2024

(54) CROWN ETHER CARBENES AND METHODS OF USE

(71) Applicant: Pall Corporation, Port Washington, NY (US)

(72) Inventors: Andrew Kocen, Port Washington, NY (US); Yiren Zhang, Port Washington, NY (US); Rehanah Sejoubsari, Port Washington, NY (US); Ahmad Arabi Shams Abadi, Port Washington, NY (US)

(73) Assignee: Pall Corporation, Port Washington, NY (US)

( * ) Notice: Subject to any disclaimer, the term of this patent is extended or adjusted under 35 U.S.C. 154(b) by 0 days.

(21) Appl. No.: 17/981,201

(22) Filed: Nov. 4, 2022

(51) Int. Cl.
*C07D 323/00* (2006.01)

(52) U.S. Cl.
CPC .................. *C07D 323/00* (2013.01)

(58) Field of Classification Search
CPC .................................................... C07D 323/00
See application file for complete search history.

(56) References Cited

U.S. PATENT DOCUMENTS

| 4,504,368 A | 3/1985 | Delton et al. |
| 5,425,878 A | 6/1995 | Lurin et al. |
| 6,468,657 B1 | 10/2002 | Hou et al. |
| 9,786,941 B2 | 10/2017 | Fuller et al. |
| 11,020,713 B2 | 6/2021 | Demeter et al. |

FOREIGN PATENT DOCUMENTS

| KR | 2019-0010382 A | 1/2019 |
| KR | 10-1987667 B1 | 6/2019 |

OTHER PUBLICATIONS

Cygan et al. Journal of Inclusion Phenomena 1988, 6, 215-220 (Year: 1988).*
Yuan et al. Makromol. Chem. 1993, 194, 1847-1862 (Year: 1993).*
Lipsky et al. Organic Syntheses, 1988, Coll. Vol. 6, p. 537 (Year: 1988).*

* cited by examiner

*Primary Examiner* — Matthew P Coughlin
(74) *Attorney, Agent, or Firm* — Leydig, Voit & Mayer, Ltd.

(57) ABSTRACT

The invention provides a material comprising (i) a crown ether of formula (I), (ii) a crown ether of formula (II), and/or (iii) a crown ether of formula (III), or a salt thereof, wherein each m independently is an integer from 1 to 8, p is an integer from 1 to 1000, each "⌇" designates an optionally present bond and/or structure, each X is an optionally present substituent, each * independently represents —H, =O, or a bond to a remainder of the material, provided that at least one * is a bond to the remainder of the material, and wherein the remainder of the material is bound via a sp3-sp3 carbon-carbon bond, a method of making the material, and a method of using the material.

20 Claims, 1 Drawing Sheet

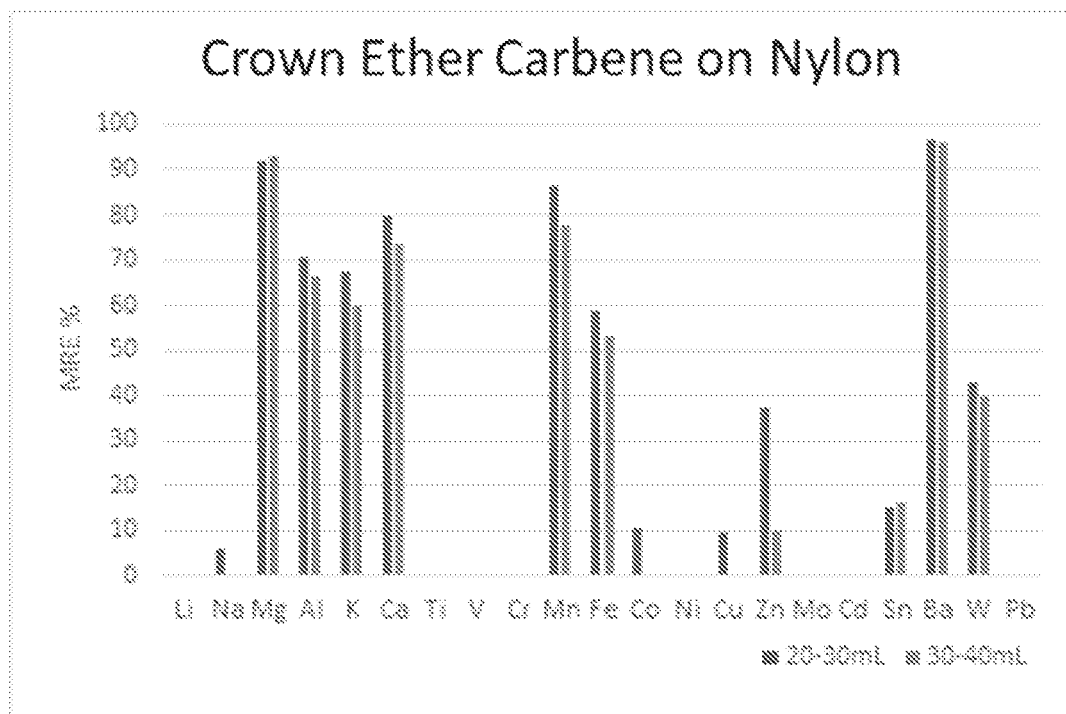

CROWN ETHER CARBENES AND METHODS OF USE

BACKGROUND OF THE INVENTION

Crown ethers are cyclic organic molecules containing oxygen- and carbon-based repeating units. Crown ethers are known to strongly bind certain cations to form a complex. In this regard, the oxygen atoms are oriented in a manner to coordinate with a metal cation located at the interior of the ring, whereas the exterior of the ring remains hydrophobic due to the repeating carbon units. As a result, the complex, including the crown ether and the cation, may be soluble in nonpolar solvents. For this reason crown ethers may be useful in phase transfer catalysis.

Due to the high utility of crown ether-based compounds there remains a need for the development of materials comprising crown ether-based compounds, as well as new and efficient ways to prepare such materials. The invention provides such materials and methods of preparation. Additional benefits and aspects of the invention will be readily apparent from the disclosure provided herein.

BRIEF SUMMARY OF THE INVENTION

The invention provides a material comprising (i) a crown ether of formula (I):

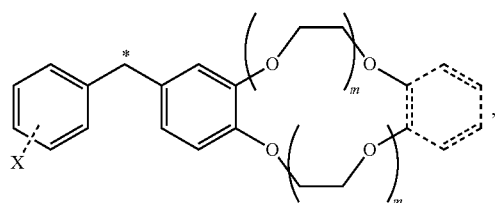

(ii) a crown ether of formula (II):

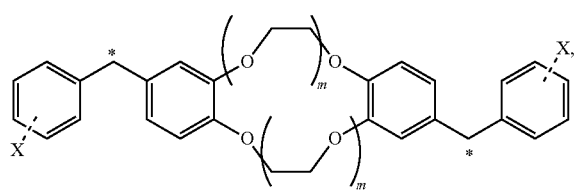

(iii) a crown ether of formula (III):

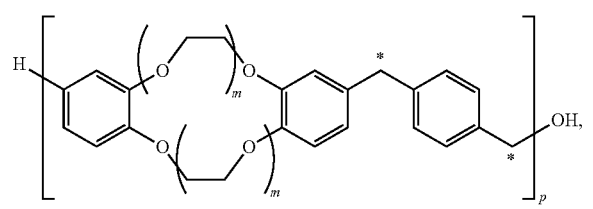

or a salt thereof, wherein each m independently is an integer from 1 to 8, p is an integer from 1 to 1000, each " " designates an optionally present bond and/or structure, each X is an optionally present substituent, each * independently represents —H, =O, or a bond to a remainder of the material, provided that at least one * is a bond to the remainder of the material, and wherein the remainder of the material is bound via a sp3-sp3 carbon-carbon bond.

The invention also provides a material of formula (IV):

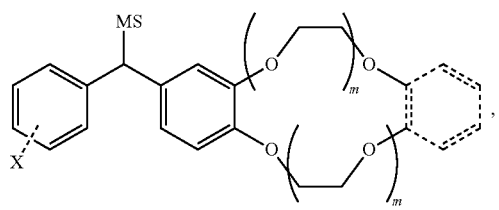

formula (V):

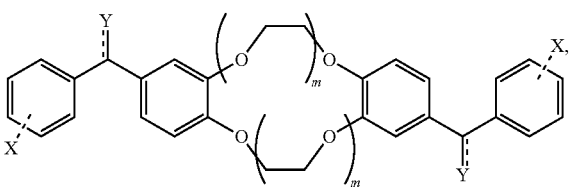

formula (VI):

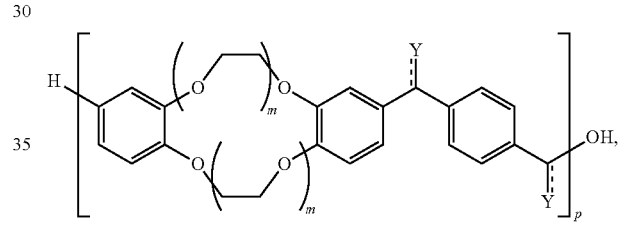

or a salt thereof, wherein each m independently is an integer from 1 to 8, p is an integer from 1 to 1000, each " " designates an optionally present bond and/or structure, each X is an optionally present substituent, each Y is hydrogen, oxygen, or MS, provided that at least one Y is MS, and each MS independently is a macromolecular support selected from a membrane, a fibrous media, a polymeric coating or material, a metal organic framework, a monolith support, a bead, a filter, or a resin, and wherein MS is bound via an sp3-sp3 carbon-carbon bond.

The invention further provides a method of making a material described herein, the method comprising (i) reacting a hydrazide or hydrazine with a crown ether of formula (VII):

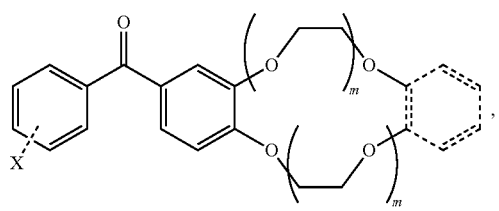

formula (VIII):

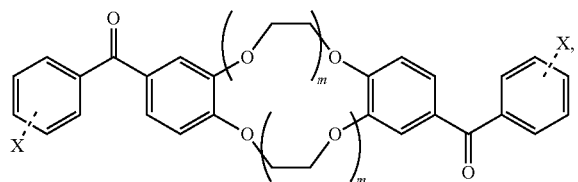

formula (IX):

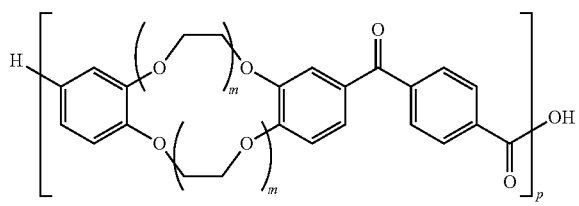

to form a hydrazone-containing compound, and (ii) reacting the hydrazone-containing compound with a macromolecular support to form at least one C—C bond.

The invention further provides a method of removing one or more metal ions from a solution comprising passing the solution through a material described herein.

BRIEF DESCRIPTION OF THE DRAWINGS

The FIGURE provides a bar graph showing the metal removal efficiency (MRE) percentage of lithium, magnesium, aluminum, potassium, calcium, titanium, vanadium, chromium, manganese, iron, cobalt, nickel, copper, zinc, molybdenum, cadmium, tin, barium, tungsten, and lead exhibited by nylon coated with a crown ether carbene, as described in Example 7.

DETAILED DESCRIPTION OF THE INVENTION

The invention provides a material comprising (i) a crown ether of formula (I):

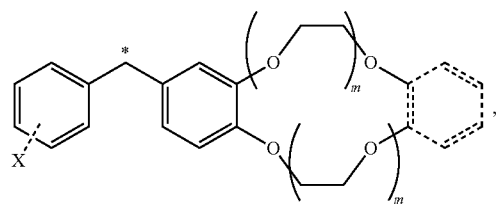

(ii) a crown ether of formula (II):

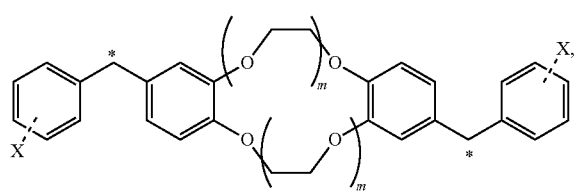

and/or (iii) a crown ether of formula (III):

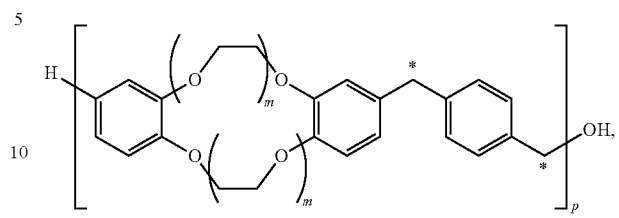

or a salt thereof, wherein each m independently is an integer from 1 to 8 (e.g., 1, 2, 3, 4, 5, 6, 7, or 8), p is an integer from 1 to 1000 (e.g., 1 to 500, 1 to 100, 10 to 50, or 1 to 10), each " $\cdots$ " designates an optionally present bond and/or structure, each X is an optionally present substituent, each * independently represents —H, =O, or a bond to a remainder of the material, provided that at least one * is a bond to the remainder of the material, and wherein the remainder of the material is bound via a sp3-sp3 carbon-carbon bond.

In some embodiments, the material comprises a crown ether of formula (I):

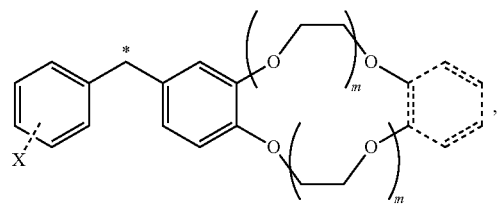

or a salt thereof, wherein each m independently is an integer from 1 to 8, each " $\cdots$ " designates an optionally present bond and/or structure, each X is an optionally present substituent, and * represents a bond to a remainder of the material, wherein the remainder of the material is bound via a sp3-sp3 carbon-carbon bond.

In some embodiments, the material comprises a crown ether of formula (II):

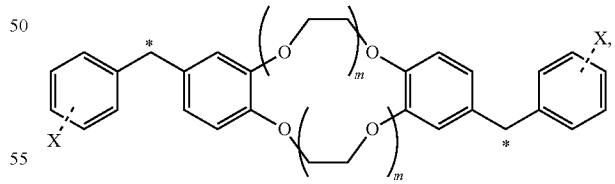

or a salt thereof, wherein each m independently is an integer from 1 to 8, each " $\cdots$ " designates an optionally present bond, each X is an optionally present substituent, each * independently represents —H, =O, or a bond to a remainder of the material, provided that at least one * is a bond to the remainder of the material, and wherein the remainder of the material is bound via a sp3-sp3 carbon-carbon bond.

In certain embodiments, the material comprises a crown ether of formula (III):

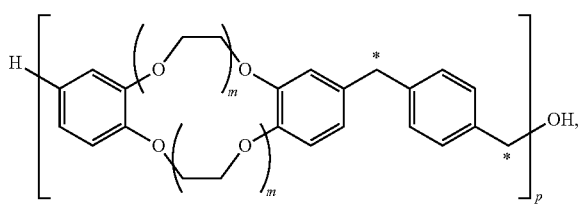

or a salt thereof, wherein each m independently is an integer from 1 to 8, p is an integer from 1 to 1000, and each * independently represents —H, =O, or a bond to a remainder of the material, provided that at least one * is a bond to the remainder of the material, and wherein the remainder of the material is bound via a sp3-sp3 carbon-carbon bond.

In any of the embodiments of the material, described herein, each m independently is an integer from 1 to 8 (e.g., 1, 2, 3, 4, 5, 6, 7, or 8). Generally, each m is selected from an integer from 1 to 8 so as to provide a crown ether selected from 12-crown-4, 15-crown-5, 18-crown-6, 21-crown-7, 24-crown-8, 27-crown-9, or 30-crown-10. For example, each m can be 2 so as to provide 12-crown-4, each m can be 3 so as to provide 18-crown-6, each m can be 4 so as to provide 24-crown-8, or each m can be 5 so as to provide 30-crown-10. Alternatively, or additionally, each m can be different so as to provide 12-crown-4, 15-crown-5, 18-crown-6, 21-crown-7, 24-crown-8, 27-crown-9, or 30-crown-10. In some embodiments, each m independently is an integer from 1 to 4. In certain embodiments, each m independently is an integer selected from 1 or 2. In other embodiments, each m is 2.

In any of the embodiments of the material, described herein, each X is an optionally present substituent. When present, X can be an electron withdrawing substituent, an electron donating substituent, or a neutral substituent. For example, each X can be independently selected from —OR, —OH, —NO$_2$, —NR$_2$, —NHR, —NH$_2$, —COOH, —F, —Cl, —Br, —I, —COOR, —CN, —R, wherein R is C1-6 alkyl (e.g., methyl, ethyl, propyl, butyl, pentyl, or hexyl). In some embodiments, no substituent "X" is present.

In any of the embodiments of the material, described herein, p is an integer from 1 to 1000 (e.g., 1 to 500, 1 to 100, 10 to 50, or 1 to 10). In some embodiments, p is an integer from 1 to 10 (e.g., 1, 2, 3, 4, 5, 6, 7, 8, 9, or 10).

In any of the embodiments of the material, described herein, each "⌇" designates an optionally present bond and/or structure. In other words, the bond to variable X is optionally present depending on whether or not substituent X is present, the bond to variable Y can be a single bond or a double bond depending on whether Y is —H, =O, or MS such that one of the bonds is optionally present, and the phenyl ring designated by the dashed lines is optionally present.

In any of the embodiments of the material described herein, each * independently represents —H, =O, or a bond to a remainder of the material, provided that at least one * is a bond to the remainder of the material, and wherein the remainder of the material is bound via a sp3-sp3 carbon-carbon bond. Without wishing to be bound by any particular theory, it is believed that the hydrazone utilized in preparing the materials described herein can (i) not be formed in the first place such that the ketone remains, (ii) hydrolyze and/or break down without undergoing a C—H insertion with the macromolecular support such that a hydrogen or ketone remains, or (iii) undergo a C—H insertion with the macromolecular support to form at least one C—C bond. In some embodiments, the material comprising a crown ether of formulae (I-III) has more than one C—C bond with the remainder of the material.

The crown ether of formulae (I)-(III) can be incorporated into any suitable material (e.g., chemical compound or media) so long as the crown ether of formulae (I)-(III) is bound to the remainder of the material via at least one carbon designated with an * in formulae (I)-(III), wherein the remainder of the material is bound via a sp3-sp3 carbon-carbon bond. It is an objective of the present application that the crown ether of formulae (I)-(III) is incorporated into the material via a C—H insertion using carbene chemistry. It will be readily understood to a person of ordinary skill in the art that the crown ether of formulae (I)-(III) can be incorporated into the material any number of times at any number of locations. Thus, the material can be any suitable material (e.g., chemical compound or media) comprising an aliphatic C—H bond available for C—H insertion. In some embodiments, the material is porous such that a liquid or fluid can be passed through the material.

In some embodiments, the remainder of the material to which the crown ether of formulae (I)-(III) is bound to a macromolecular support selected from a membrane (e.g., a porous membrane or a permeable membrane), a fibrous media, a polymeric coating (e.g., a laminate or sealant such as a polyurethane coating, an epoxy coating, an acrylic coating, etc.) or material (e.g., gelatin, alginate, starch, polyethylene, polypropylene, nylon, polyvinylidene fluoride, polyethylene oxide, polypropylene oxide, polyethylene/polypropylene oxide, polyacrylonitrile, poly(meth)acrylate, poly(meth)acrylamide, polyamide, polyimide, polyester, cellulose, polystyrene, etc.), a metal organic framework, a monolith support (e.g., a catalyst support), a bead (e.g., a polymeric bead), a filter, or a resin (e.g., a chromatographic resin). In some embodiments, the macromolecular support comprises gelatin, alginate, starch, polyethylene (e.g., high density polyethylene), polypropylene, nylon, polyvinylidene fluoride, polyethylene oxide, polypropylene oxide, polyethylene/polypropylene oxide, polyacrylonitrile, poly(meth)acrylate, poly(meth)acrylamide, polyamide (e.g., nylon), polyimide, polyester, cellulose, polystyrene, or a combination thereof. In certain embodiments, the macromolecular support comprises polyethylene, polypropylene, nylon, polyvinylidene fluoride, polyethylene oxide, polypropylene oxide, polyethylene/polypropylene oxide, polyacrylonitrile, cellulose, or a combination thereof.

Thus, in some embodiments, the material is of formula (IV):

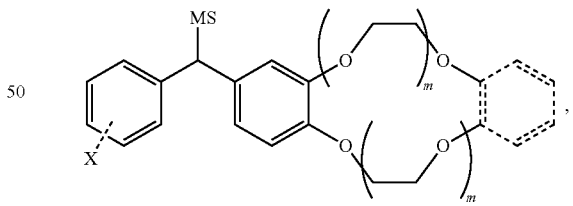

formula (V):

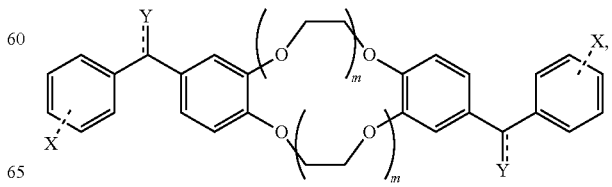

or formula (VI):

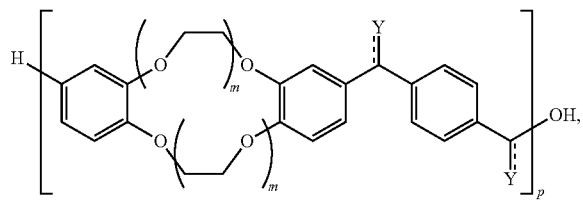

or a salt thereof, wherein each m independently is an integer from 1 to 8, p is an integer from 1 to 1000, each " ⌒ " designates an optionally present bond and/or structure, each X is an optionally present substituent, each Y is hydrogen, oxygen, or MS, provided that at least one Y is MS, and each MS independently is a macromolecular support selected from a membrane, a fibrous media, a polymeric coating or material, a metal organic framework, a monolith support, a bead, a filter, or a resin, and wherein MS is bound via an sp3-sp3 carbon-carbon bond. All other definitions and embodiments, with respect to variables m, p, and X and the macromolecular support are as described herein with respect to the inventive material.

In any of the embodiments of the material described herein, each Y is hydrogen, oxygen, or MS, provided that at least one Y is MS, wherein MS is bound via an sp3-sp3 carbon-carbon bond. Without wishing to be bound by any particular theory, it is believed that the hydrazone utilized in preparing the materials described herein can (i) not be formed in the first place such that the ketone remains, (ii) hydrolyze and/or break down without undergoing a C—H insertion with the macromolecular support such that a hydrogen or ketone remains, or (iii) undergo a C—H insertion with the macromolecular support to form at least one C-MS bond via an sp3-sp3 carbon-carbon bond. In some embodiments, the material of formulae (IV-VI) has more than one C-MS bond.

In some embodiments, the material is of formula (IV):

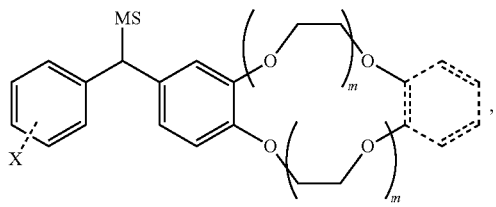

or a salt thereof, wherein each m independently is an integer from 1 to 8, each " ⌒ " designates an optionally present bond and/or structure, each X is an optionally present substituent, and MS is a macromolecular support selected from a membrane, a fibrous media, a polymeric coating or material, a metal organic framework, a monolith support, a bead, a filter, or a resin, and wherein MS is bound via an sp3-sp3 carbon-carbon bond. All other definitions and embodiments, with respect to variables m and X and the macromolecular support are as described herein with respect to the inventive material.

In other embodiments, the material is of formula (V):

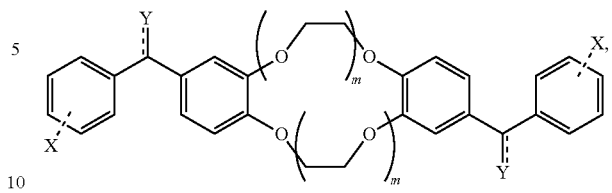

or a salt thereof, wherein each m independently is an integer from 1 to 8, each " ⌒ " designates an optionally present bond, each X is an optionally present substituent, each Y is hydrogen, oxygen, or MS, provided that at least one Y is MS, and each MS independently is a macromolecular support selected from a membrane, a fibrous media, a polymeric coating or material, a metal organic framework, a monolith support, a bead, a filter, or a resin, and wherein MS is bound via an sp3-sp3 carbon-carbon bond. All other definitions and embodiments, with respect to variables m, X, and Y and the macromolecular support are as described herein with respect to the inventive material.

In certain embodiments, the material is of formula (VI):

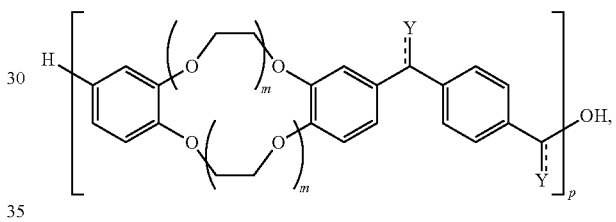

or a salt thereof, wherein each m independently is an integer from 1 to 8, p is an integer from 1 to 1000, each " ⌒ " designates an optionally present bond and/or structure, each Y is hydrogen, oxygen, or MS, provided that at least one Y is MS, and each MS independently is a macromolecular support selected from a membrane, a fibrous media, a polymeric coating or material, a metal organic framework, a monolith support, a bead, a filter, or a resin, and wherein MS is bound via an sp3-sp3 carbon-carbon bond. All other definitions and embodiments, with respect to variables m, p, and Y and the macromolecular support are as described herein with respect to the inventive material.

It is an objective of the present application that the crown ether of formulae (I)-(III) is incorporated into the material via a C—H insertion using carbene chemistry. Thus, the invention also provides a method of making a material described, the method comprising:

(i) reacting a hydrazide or hydrazine with a crown ether of formula (VII):

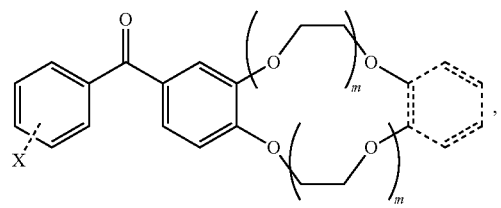

formula (VIII):

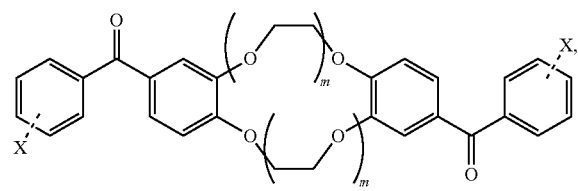

or formula (IX):

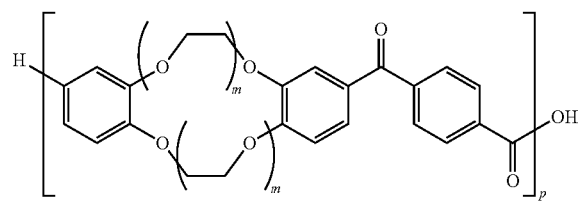

to form a hydrazone-containing compound, and
   (ii) reacting the hydrazone-containing compound with a macromolecular support selected from a membrane, a fibrous media, a polymeric coating or material, a metal organic framework, a monolith support, a bead, a filter, or a resin to form at least one C—C bond. All other definitions and embodiments, with respect to variables m, p, and X and the macromolecular support are as described herein with respect to the inventive material.

The method comprises reacting a hydrazide or hydrazine with a crown ether of formulae (VII)-(VIII). For example, the hydrazide or hydrazine can be combined (e.g., contacted), mixed (e.g., shaken, stirred, etc.) heated, refluxed, or a combination thereof with the crown ether of formulae (VII)-(VIII) for any duration of time so long as the desired hydrazone-containing compound is formed.

The hydrazide or hydrazine can be any suitable hydrazide or hydrazine known to a person of ordinary skill in the art, so long as the hydrazide or hydrazine, when in the form of a hydrazone-containing compound, is capable of breaking down to form a reactive carbene. For example, the hydrazide or hydrazine can be p-toluenesulfonyl hydrazide (i.e., tosylhydrazide), benzenesulfonyl hydrazide, 2,4,6-triisopropylbenzenesulfonyl hydrazide, or the like. In some embodiment, the hydrazide or hydrazine is p-toluenesulfonyl hydrazide.

The hydrazide or hydrazine can be used in any suitable amount. Generally, the hydrazide or hydrazine is added in slight excess (e.g., about 1 molar equivalent, about 1.05 molar equivalents, about 1.1 molar equivalent, about 1.15 molar equivalents, or about 1.2 molar equivalents) to the number of hydrazone moieties desired. Thus, in some embodiments, the hydrazide or hydrazine is added in an amount of at least 1×, at least 1.05×, at least 1.1×, at least 1.15×, or at least 1.2× molar equivalents relative to the number of hydrazone moieties desired.

In some embodiments, the formation of the hydrazone-containing compound is formed in a solvent. Thus, the reaction between the hydrazide or hydrazine and the crown ether of formulae (VII)-(VIII) can be performed in any suitable solvent. In some embodiments, the solvent is a high boiling solvent (i.e., greater than 100° C.) such as toluene or the like. However, the formation of the hydrazone-containing compound can also be carried out in a low boiling solvent (i.e., less than 100° C.) such as ethanol, methanol, or the like if facilitated by an acid promoter.

In some embodiments, the formation of the hydrazone-containing compound is facilitated by an acid promoter and/or heat. The acid promoter can be any suitable Brønsted acid or Lewis acid. For example, the formation of the hydrazone-containing compound can be facilitated by p-toluenesulfonic acid, acetic acid, or formic acid. The reaction can be heated to any suitable temperature. Since the goal is to drive off water, in some embodiments, the reaction between the hydrazide or hydrazine and the crown ether of formulae (VII)-(VIII) is heated to a temperature of greater than 100° C., for example, by using a Dean-Stark apparatus.

The method further comprises reacting the hydrazone-containing compound with a macromolecular support selected from a membrane, a fibrous media, a polymeric coating or material, a metal organic framework, a monolith support, a bead, a filter, or a resin to form at least one C—C bond. For example, the hydrazone-containing compound can be combined (e.g., contacted), mixed (e.g., shaken, stirred, etc.) heated, refluxed, or a combination thereof with the macromolecular support for any duration of time so long as the desired C—C bond is formed.

In some embodiments, the C—C bond is formed in a solvent. Thus, the reaction between the hydrazone-containing compound and the macromolecular support can be performed in any suitable solvent (e.g., organic solvent). For example, the reaction between the hydrazone-containing compound and the macromolecular support can be performed in ethanol, N-methyl-2-pyrrolidone, dimethylformamide, dimethylacetamide, methanol, isopropyl alcohol, tetrahydrofuran, acetonitrile, or a combination thereof.

In some embodiments, the reaction between the hydrazone-containing compound and the macromolecular support is facilitated by a base promoter. In other words, the formation of the carbene can be facilitated by a base promoter. The base promoter can be any suitable Brønsted base or Lewis base. For example, the base promoter can be sodium hydroxide, potassium hydroxide, tetramethylammonium hydroxide, potassium tert-butoxide, or a combination thereof. In certain embodiments the reaction between the hydrazone-containing compound and the macromolecular support is carried out in ethanol and/or N-methyl-2-pyrrolidone in the presence of sodium hydroxide.

The base promoter can be used in any suitable amount. Generally, the base promoter is added in excess (e.g., at least about 1 molar equivalent, at least about 2 molar equivalents, at least about 5 molar equivalents, or at least about 10 molar equivalents) to the number of hydrazone moieties present in the reacting hydrazone-containing molecule. Thus, in some embodiments, the base promoter is added in an amount of at least 1×, at least 2×, at least 5×, at least 10×, molar equivalents to the number of hydrazone moieties present in the reacting hydrazone-containing molecule.

In some embodiments, the formation of the carbene is further facilitated by a metal catalyst. Metal catalysts suitable for the formation and/or stabilization of carbene moieties are known in the art. For example, the formation of the carbene can be facilitated by a copper catalyst, a rhodium catalyst, an iron catalyst, a ruthenium catalyst, a molybdenum catalyst, or a combination thereof. In certain embodiments, the reaction between the hydrazone-containing compound and the macromolecular support does not contain a metal catalyst.

The reaction between the hydrazone-containing compound and the macromolecular support can be heated and/or subjected to ultraviolet (UV) light. Without wishing to be bound by any particular theory, it is believed that the formation of the C—C bond (e.g., via C—H insertion) may be facilitated by increased temperature (e.g., greater than 50° C. or greater than 75° C.) and/or UV light. In certain embodiments, the reaction between the hydrazone-containing compound and the macromolecular support is cured using patterned selective functionalization with UV light exposure.

The materials described herein can be used in any suitable industrial application for any suitable purpose. For example, the materials described herein can be used in water purification applications, wastewater treatment applications, mining applications, electronic (e.g., microelectronic) applications, papermaking applications, pharmaceutical applications, biomedical applications, energy applications (e.g., as separators in fuel cells or batteries), or metallurgy applications. Generally, the materials described herein are used to selectively remove one or more metal ions from a fluid (i.e., solution). The fluid can be any suitable liquid containing a solvent (e.g., water, alcohols, sulfoxides, sulfides, acetates, ethers, amides, nitriles, or a combination thereof) and one or more metal ions. In certain embodiments, the fluid (i.e., solution) is an aqueous solution.

In some embodiments, the materials described herein can be used in a method of removing one or more metal ions from a solution comprising passing the solution through the material. For example, the material can be used as a filter, porous media, chromatographic resin, membrane, or the like through which the solution passes to remove one or more metal ions. Thus, the invention further provides a method of removing one or more metal ions from a solution comprising passing the solution through a material comprising (i) a crown ether of formula (I):

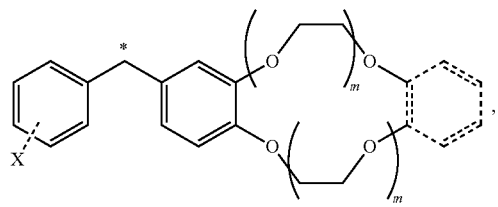

(ii) a crown ether of formula (II):

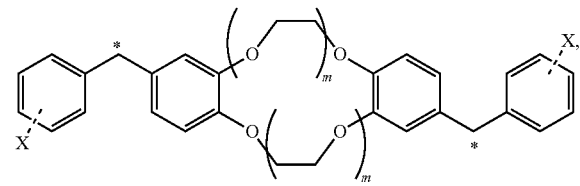

and/or
(iii) a crown ether of formula (III):

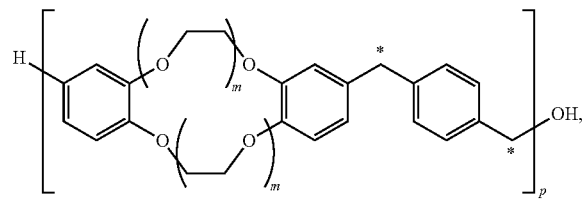

or a salt thereof, wherein each m independently is an integer from 1 to 8 (e.g., 1, 2, 3, 4, 5, 6, 7, or 8), p is an integer from 1 to 1000 (e.g., 1 to 500, 1 to 100, 10 to 50, or 1 to 10), each "$\cdots$" designates an optionally present bond and/or structure, each X is an optionally present substituent, each * independently represents —H, =O, or a bond to a remainder of the material, provided that at least one * is a bond to the remainder of the material, and wherein the remainder of the material is bound via a sp3-sp3 carbon-carbon bond. All other definitions and embodiments, with respect to variables m, p, X, and Y and the macromolecular support are as described herein with respect to the inventive material.

The method can be used to remove any suitable ion. Alternatively, or additionally, the method can be used to allow any suitable ion to pass through the material. For example, the method can used to selectively remove one or more metal ions selected from sodium, magnesium, aluminum, potassium, calcium, titanium, vanadium, chromium, manganese, iron, cobalt, nickel, copper, zinc, molybdenum, cadmium, tin, barium, tungsten, lead, or a combination thereof. Alternatively, or additionally, the method can be used to selectively allow one or more metal ions selected from sodium, magnesium, aluminum, potassium, calcium, titanium, vanadium, chromium, manganese, iron, cobalt, nickel, copper, zinc, molybdenum, cadmium, tin, barium, tungsten, lead, or a combination thereof through the material. In certain embodiments, the method selectively allows for lithium to pass through the material and removes one or more metal ions selected from sodium, magnesium, aluminum, potassium, calcium, titanium, vanadium, chromium, manganese, iron, cobalt, nickel, copper, zinc, molybdenum, cadmium, tin, barium, tungsten, lead, or a combination thereof.

The method can remove any suitable amount of the one or more metal ions from the solution. For example, the method can remove at least 40% of the one or more metal ions from the solution, at least 50% of the one or more metal ions from the solution, at least 60% of the one or more metal ions from the solution, at least 70% of the one or more metal ions from the solution, at least 80% of the one or more metal ions from the solution, or at least 90% of the one or more metal ions from the solution. In some embodiments, the method removes at least 50% of one or more metal ions selected from sodium, magnesium, aluminum, potassium, calcium, titanium, vanadium, chromium, manganese, iron, cobalt, nickel, copper, zinc, molybdenum, cadmium, tin, barium, tungsten, lead, or a combination thereof. In certain embodiments, the method removes at least 60% of one or more metal ions selected from sodium, magnesium, aluminum, potassium, calcium, titanium, vanadium, chromium, manganese, iron, cobalt, nickel, copper, zinc, molybdenum, cadmium, tin, barium, tungsten, lead, or a combination thereof. In preferred embodiments, the method removes at least 70% of one or more metal ions selected from sodium, magnesium, aluminum, potassium, calcium, titanium, vanadium, chromium, manganese, iron, cobalt, nickel, copper, zinc, molybdenum, cadmium, tin, barium, tungsten, lead, or a combination thereof.

In some embodiments, the solution that passes through the material is the desirable product of the methods described herein. Thus, in such embodiments, the method can further comprise recovering the solution (e.g., aqueous solution) that has been passed through the material. Without wishing to be bound by any particular theory, it is believed that when smaller metal ions such as lithium and/or sodium are desired, the recovered solution will be the desired product since smaller metal ions such as lithium and/or sodium are more likely to pass through the materials described herein.

In other embodiments, the one or more metal ions removed from the solution are the desirable product of the method described herein. Thus, in these embodiments, the method can further comprise recovering the one or more metal ions removed from the solution. The one or more metal ions can be recovered by any suitable means. For example the material containing the one or more metal ions can be washed with a recovery solution. Without wishing to be bound by any particular theory, it is believed that when larger metal ions such as magnesium, aluminum, potassium, calcium, manganese, iron, barium, etc. are desired, these desired metal ions will remain in the material because larger metal ions are less likely to pass through the materials described herein.

Aspects, including embodiments, of the invention described herein may be beneficial alone or in combination, with one or more other aspects or embodiments. Without limiting the foregoing description, certain non-limiting embodiments of the disclosure numbered 1-22 are provided below. As will be apparent to those of skill in the art upon reading this disclosure, each of the individually numbered embodiments may be used or combined with any of the preceding or following individually numbered embodiments. This is intended to provide support for all such combinations of embodiments and is not limited to combinations of embodiments explicitly provided below:

EMBODIMENTS (1) In embodiment (1) is presented a material comprising (i) a crown ether of formula (I):

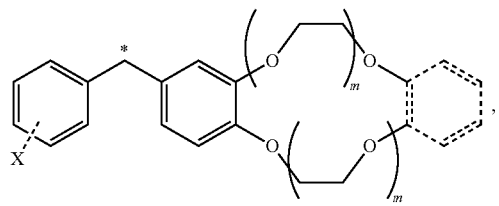

(ii) a crown ether of formula (II):

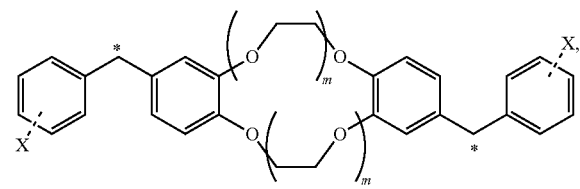

and/or
(iii) a crown ether of formula (III):

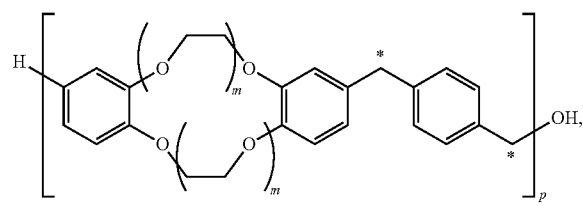

or a salt thereof, wherein each m independently is an integer from 1 to 8, p is an integer from 1 to 1000, each " $\cdots$ " designates an optionally present bond and/or structure, each X is an optionally present substituent, each * independently represents —H, =O, or a bond to a remainder of the material, provided that at least one * is a bond to the remainder of the material, and wherein the remainder of the material is bound via a sp3-sp3 carbon-carbon bond.

(2) In embodiment (2) is presented the material of embodiment (1), wherein the material comprises a crown ether of formula (I):

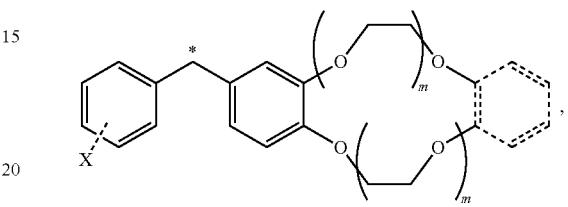

or a salt thereof, wherein each m independently is an integer from 1 to 8, each " $\cdots$ " designates an optionally present bond and/or structure, each X is an optionally present substituent, and * represents a bond to a remainder of the material, wherein the remainder of the material is bound via a sp3-sp3 carbon-carbon bond.

(3) In embodiment (3) is presented the material of embodiment (1), wherein the material comprises a crown ether of formula (II):

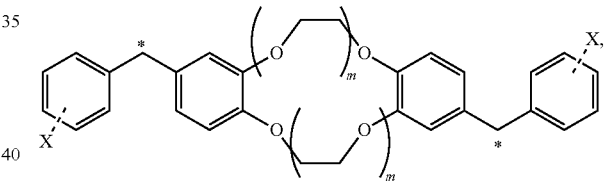

or a salt thereof, wherein each m independently is an integer from 1 to 8, each " $\cdots$ " designates an optionally present bond, each X is an optionally present substituent, each * independently represents —H, =O, or a bond to a remainder of the material, provided that at least one * is a bond to the remainder of the material, and wherein the remainder of the material is bound via a sp3-sp3 carbon-carbon bond.

(4) In embodiment (4) is presented the material of embodiment (1), wherein the material comprises a crown ether of formula (III):

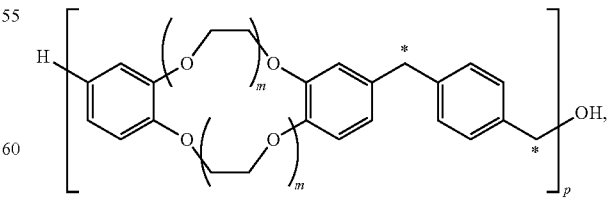

or a salt thereof, wherein each m independently is an integer from 1 to 8, p is an integer from 1 to 1000, and each * independently represents —H, =O, or a bond to a remainder of the material, provided that at least one * is a bond to the remainder of the material, and wherein the remainder of the material is bound via a sp3-sp3 carbon-carbon bond.

(5) In embodiment (5) is presented the material of embodiments (1)-(4), wherein each m independently is an integer from 1 to 4.

(6) In embodiment (6) is presented the material of any one of embodiments (1)-(5), wherein each m independently is an integer selected from 1 or 2.

(7) In embodiment (7) is presented the material of any one of embodiments (1)-(6), wherein each m is 2.

(8) In embodiment (8) is presented the material of embodiment (1), wherein the material is of formula (IV):

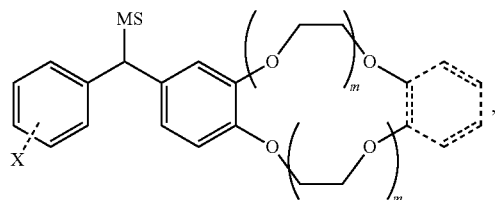

formula (V):

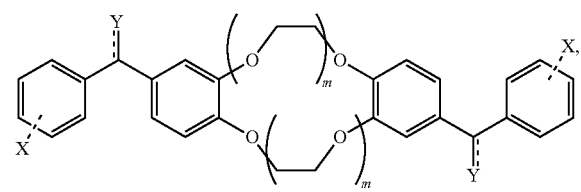

formula (VI):

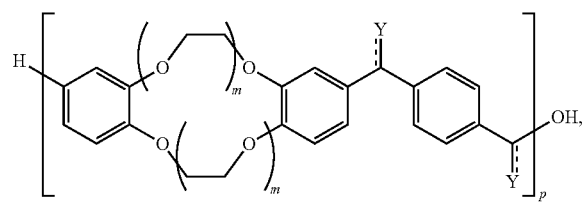

or a salt thereof, wherein each m independently is an integer from 1 to 8, p is an integer from 1 to 1000, each "⌇" designates an optionally present bond and/or structure, each X is an optionally present substituent, each Y is hydrogen, oxygen, or MS, provided that at least one Y is MS, and each MS independently is a macromolecular support selected from a membrane, a fibrous media, a polymeric coating or material, a metal organic framework, a monolith support, a bead, a filter, or a resin, and wherein MS is bound via an sp3-sp3 carbon-carbon bond.

(9) In embodiment (9) is presented the material of embodiment (8), wherein the material is of formula (IV):

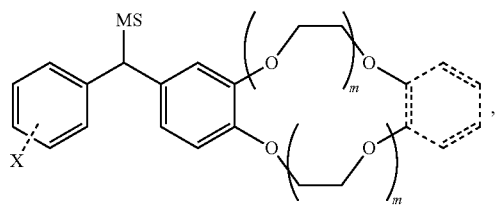

or a salt thereof, wherein each m independently is an integer from 1 to 8, each "⌇" designates an optionally present bond and/or structure, each X is an optionally present substituent, and MS is a macromolecular support selected from a membrane, a fibrous media, a polymeric coating or material, a metal organic framework, a monolith support, a bead, a filter, or a resin, and wherein MS is bound via an sp3-sp3 carbon-carbon bond.

(10) In embodiment (10) is presented the material of embodiment (8), wherein the material is of formula (V):

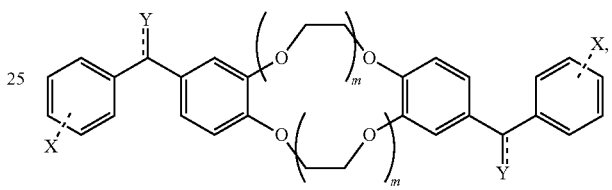

or a salt thereof, wherein each m independently is an integer from 1 to 8, each "⌇" designates an optionally present bond, each X is an optionally present substituent, each Y is hydrogen, oxygen, or MS, provided that at least one Y is MS, and each MS independently is a macromolecular support selected from a membrane, a fibrous media, a polymeric coating or material, a metal organic framework, a monolith support, a bead, a filter, or a resin, and wherein MS is bound via an sp3-sp3 carbon-carbon bond.

(11) In embodiment (11) is presented the material of embodiment (8), wherein the material is of formula (VI):

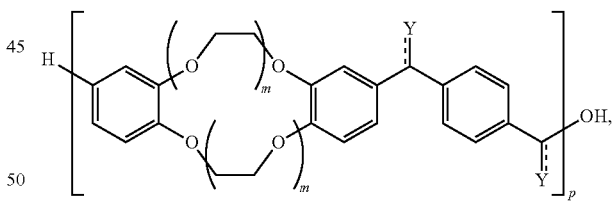

or a salt thereof, wherein each m independently is an integer from 1 to 8, p is an integer from 1 to 1000, each "⌇" designates an optionally present bond and/or structure, each Y is hydrogen, oxygen, or MS, provided that at least one Y is MS, and each MS independently is a macromolecular support selected from a membrane, a fibrous media, a polymeric coating or material, a metal organic framework, a monolith support, a bead, a filter, or a resin, and wherein MS is bound via an sp3-sp3 carbon-carbon bond.

(12) In embodiment (12) is presented the material of any one of embodiments (8)-(11), wherein each m independently is an integer from 1 to 4.

(13) In embodiment (13) is presented the material of any one of embodiments (8)-(12), wherein each m independently is an integer selected from 1 or 2.

(14) In embodiment (14) is presented the material of any one of embodiments (8)-(13), wherein each m is 2.

(15) In embodiment (15) is presented the material of any one of embodiments (8)-(14), wherein the macromolecular support comprises gelatin, alginate, starch, polyethylene, polypropylene, nylon, polyvinylidene fluoride, polyethylene oxide, polypropylene oxide, polyethylene/polypropylene oxide, polyacrylonitrile, poly(meth)acrylate, poly(meth)acrylamide, polyamide, polyimide, polyester, cellulose, polystyrene, or a combination thereof.

(16) In embodiment (16) is presented a method of making a material of any one of embodiments (8)-(15), the method comprising:
(i) reacting a hydrazide or hydrazine with a crown ether of formula (VII):

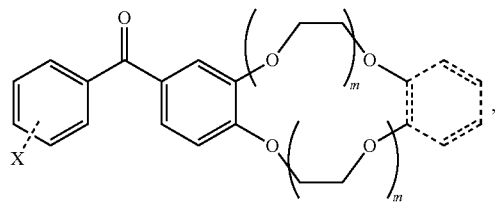

formula (VIII):

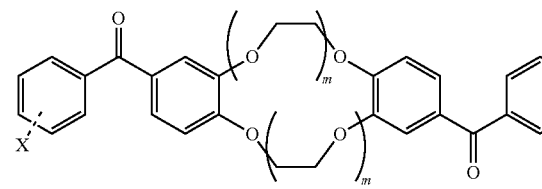

or formula (IX):

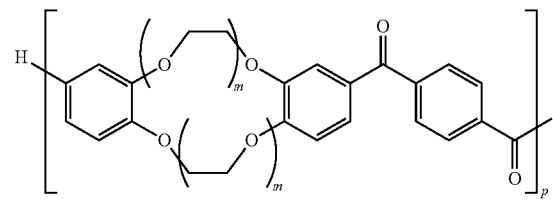

to form a hydrazone-containing compound, and
(ii) reacting the hydrazone-containing compound with a macromolecular support selected from a membrane, a fibrous media, a polymeric coating or material, a metal organic framework, a monolith support, a bead, a filter, or a resin to form at least one C—C bond.

(17) In embodiment (17) is presented the method of embodiment (16), wherein the hydrazide or hydrazine is p-toluenesulfonyl hydrazide.

(18) In embodiment (18) is presented a method of removing one or more metal ions from a solution comprising passing the solution through the material of any one of embodiments (1)-(15), or a salt thereof.

(19) In embodiment (19) is presented the method of embodiment (18), wherein the solution is an aqueous solution.

(20) In embodiment (20) is presented the method of embodiment (18) or embodiment (19), wherein the method removes at least 50% of one or more metal ions selected from sodium, magnesium, aluminum, potassium, calcium, titanium, vanadium, chromium, manganese, iron, cobalt, nickel, copper, zinc, molybdenum, cadmium, tin, barium, tungsten, lead, or a combination thereof.

(21) In embodiment (22) is presented the method of embodiment (18) or embodiment (19), wherein the method removes at least 60% of one or more metal ions selected from sodium, magnesium, aluminum, potassium, calcium, titanium, vanadium, chromium, manganese, iron, cobalt, nickel, copper, zinc, molybdenum, cadmium, tin, barium, tungsten, lead, or a combination thereof.

(22) In embodiment (22) is presented the method of embodiment (18) or embodiment (19), wherein the method removes at least 70% of one or more metal ions selected from sodium, magnesium, aluminum, potassium, calcium, titanium, vanadium, chromium, manganese, iron, cobalt, nickel, copper, zinc, molybdenum, cadmium, tin, barium, tungsten, lead, or a combination thereof.

EXAMPLES

These following examples further illustrate the invention but, of course, should not be construed as in any way limiting its scope.

Example 1

This example provides an exemplary experimental procedure for the preparation of a crown ether of formula (VII), described herein, which is summarized in Scheme 1.

Scheme 1.

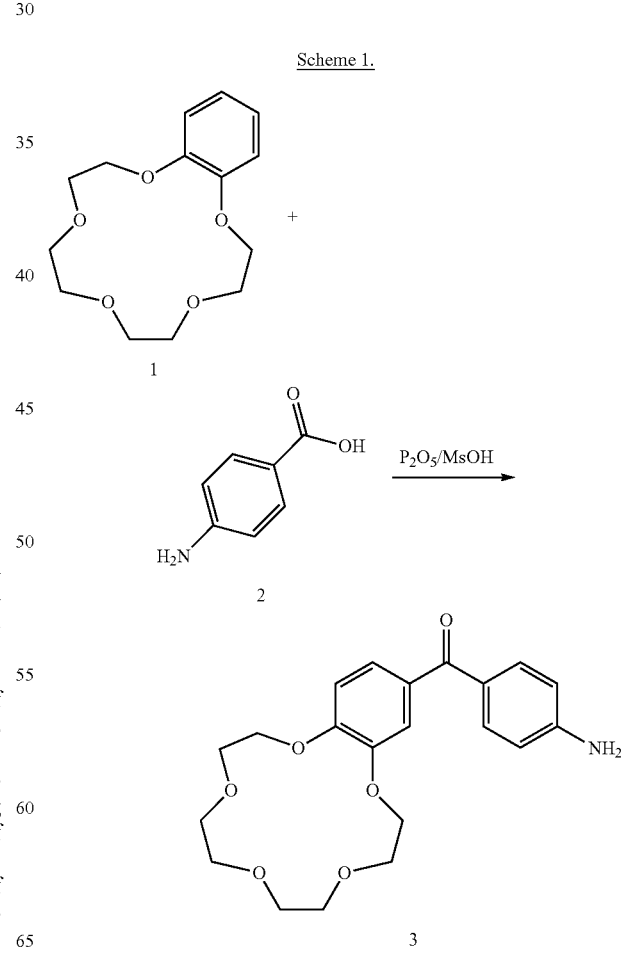

Benzo crown ether 1 (5 g, 18.6 mmol, 1 eq) was dissolved in Eaton's Reagent (35 g) at 50° C. Once fully dissolved, 4-aminobenzoic acid 2 (2.8 g, 20.5 mmol, 1.1 eq) was added and the reaction was heated at 50° C. for 16 hours. The resulting mixture was poured onto ice, filtered, and washed with water. After allowing the resulting solid product to dry on the filter, the product was recrystallized from ethanol to yield 2.23 g (31%) of aminobenzo crown ether 3.

Example 2

This example provides an exemplary experimental procedure for the preparation of a crown ether of formula (VII), described herein, which is summarized in Scheme 2.

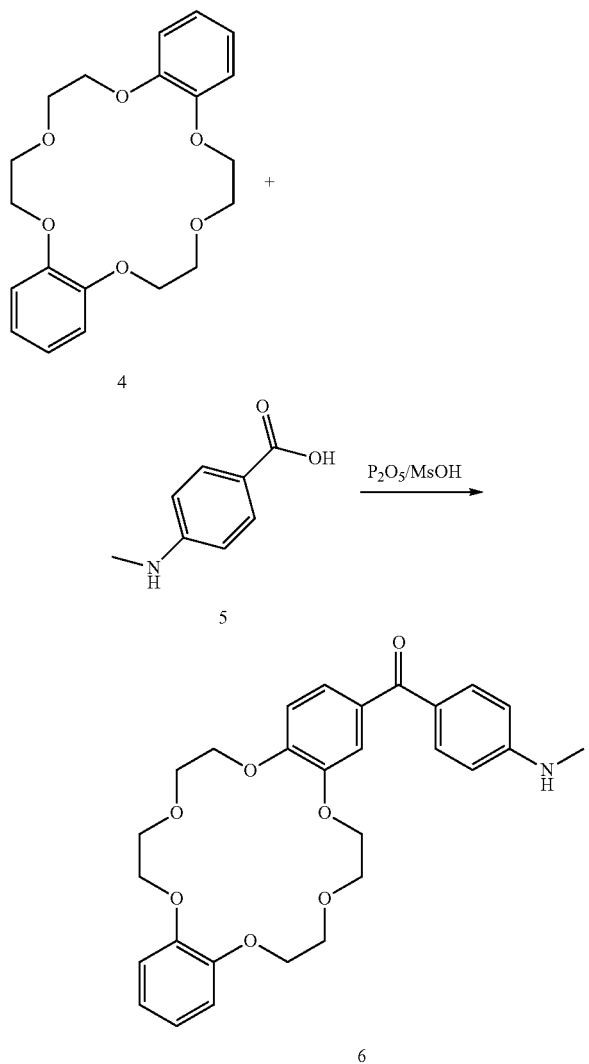

Dibenzo crown ether 4 (24.0 g, 66.5 mmol) was dissolved in Eaton's Reagent (110 mL) at 50° C. Once fully dissolved, 4-(methylamino)benzoic acid 5 (10.0 g, 66.5 mmol, 1 eq) was added and the reaction was heated at 50° C. for 4 hours. The resulting mixture was poured onto ice, filtered, and washed with water. After allowing the resulting solid product to dry on the filter, crude aminodibenzo crown ether 6 (30 g) was recovered. Nuclear magnetic resonance (NMR) spectroscopy indicated that the crude product was >85% of the desired product 6, with the mass balance being a mixture of starting material 4 and the double addition product.

Example 3

This example provides an exemplary experimental procedure for the preparation of a crown ether of formula (VIII), described herein, which is summarized in Scheme 3.

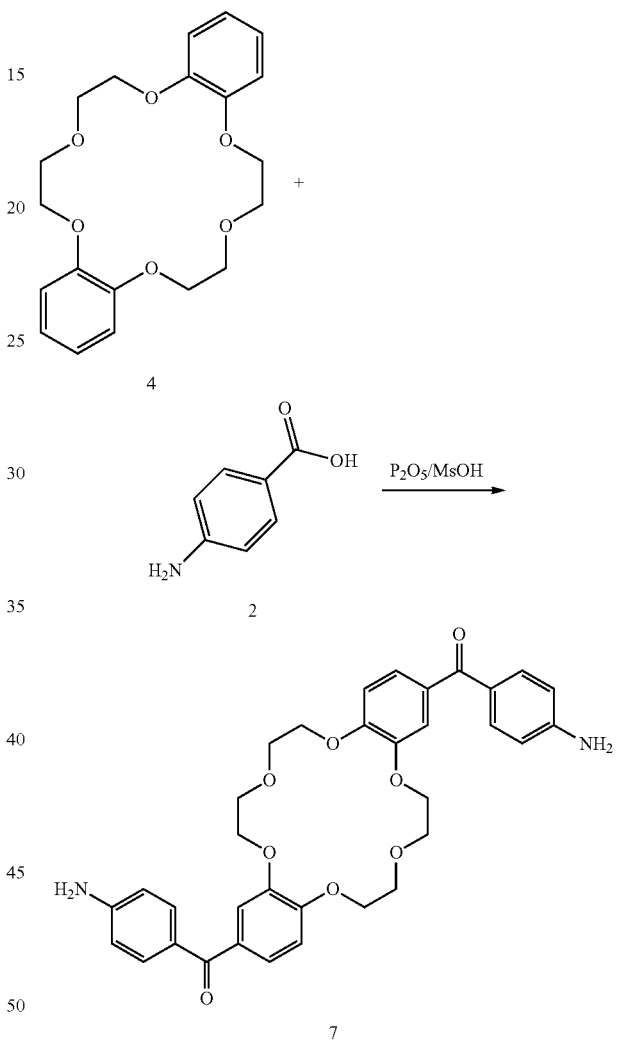

Dibenzo crown ether 4 (5.0 g, 13.8 mmol, 1 eq) was dissolved in Eaton's Reagent (35 g) at 50° C. Once fully dissolved, 4-aminobenzoic acid 2 (4.16 g, 30.4 mmol, 2.2 eq) was added and the reaction was heated at 50° C. for 4 hours. The resulting mixture was poured onto ice, filtered, and washed with water. After allowing the resulting solid product to dry on the filter, the product was recrystallized from ethanol to yield 4.1 g (50%) of diaminodibenzo crown ether 7.

Example 4

This example provides an exemplary experimental procedure for the preparation of a crown ether of formula (VIII), described herein, which is summarized in Scheme 4.

Scheme 4.

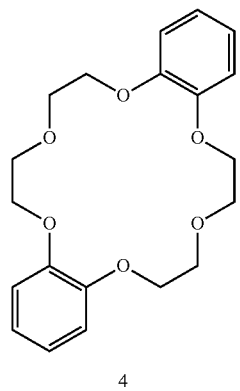

4

+

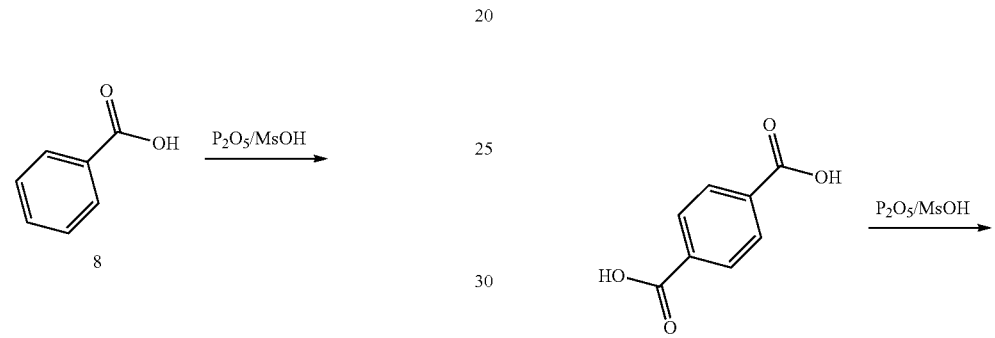

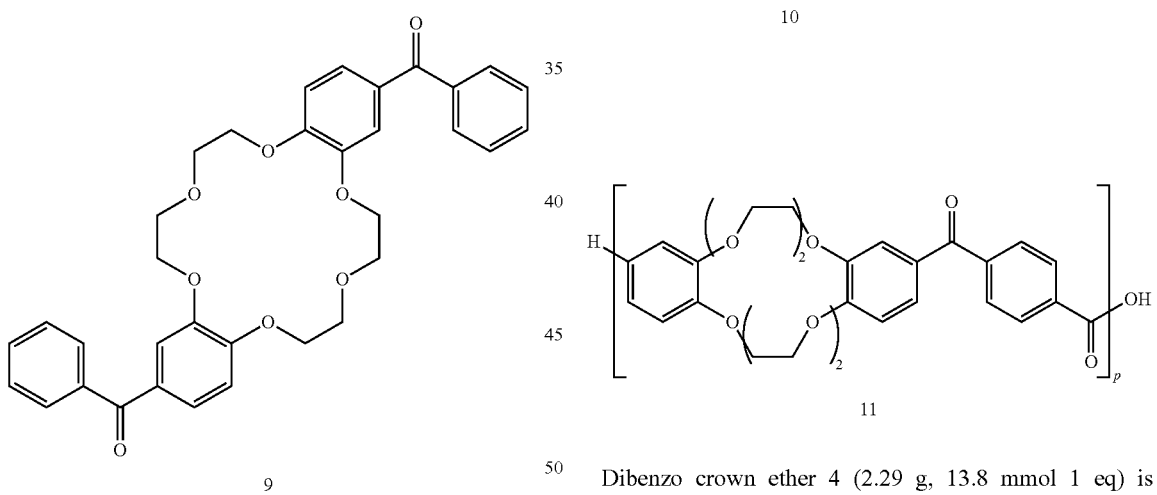

9

Dibenzo crown ether 4 (5.0 g, 13.8 mmol, 1 eq) was dissolved in Eaton's Reagent (35 g) at 50° C. Once fully dissolved, benzoic acid 8 (3.71 g, 30.4 mmol, 2.2 eq) was added and the reaction was heated at 50° C. for 4 hours. The resulting mixture was poured onto ice, filtered, and washed with water. After allowing the resulting solid product to dry on the filter, the product was recrystallized from ethanol to yield 7.25 g (92%) of dibenzoic-benzo-18-crown-6 (9).

Example 5

This example provides an exemplary experimental procedure for the preparation of a crown ether of formula (IX), described herein, which is summarized in Scheme 5.

Scheme 5.

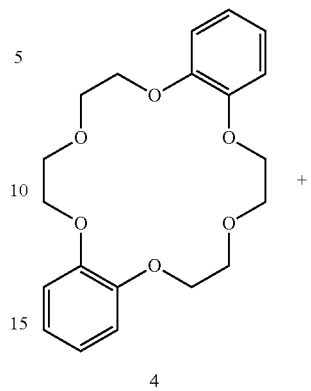

4

+

Dibenzo crown ether 4 (2.29 g, 13.8 mmol 1 eq) is dissolved in Eaton's Reagent (70 g) at 50° C. Once fully dissolved, 1,4-benzendicarboxylic acid 10 (5.00 g, 13.8 mmol, 1 eq) is added and the reaction is heated at 50° C. for 4 hours. The resulting mixture is poured onto ice, filtered, and washed with water and then methanol. After allowing the resulting solid product to dry on the filter, 4.21 g (62%) of the polymeric product 11 is recovered with a degree of polymerization of approximately 20, as approximated using nuclear magnetic resonance (NMR) spectroscopy.

Example 6

This example provides an exemplary experimental procedure for the preparation of a material of formula (V), described herein, the first step of which is summarized in Scheme 6.

Scheme 6.

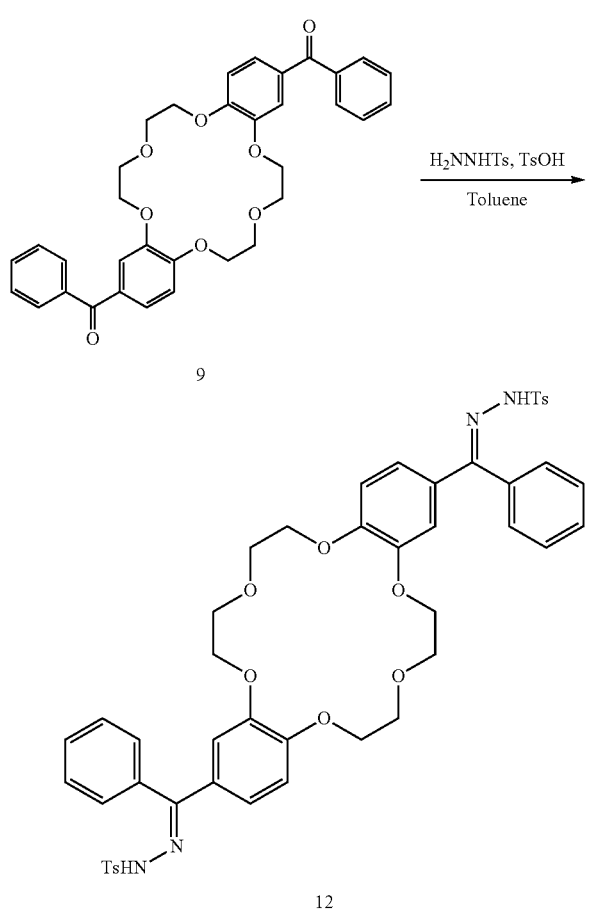

Dibenzoic-benzo-18-crown-6 (9) (3.52 g, 6 mmol, 1 eq), p-toluenesulfonyl (i.e., tosyl) hydrazide (2.23 g, 12 mmol, 2 eq), and p-toluenesulfonic acid (10 mg, 1 mol %) were heated in toluene (100 mL) with a Dean-Stark trap at reflux for 16 hours. The resulting mixture was cooled in a freezer and filtered to give a powder, which was washed with ethanol and then dried. Nuclear magnetic resonance (NMR) spectroscopy was used to confirm the desirable conversion to the imine with a yield of approximately 76% of crude product 12. The isolated hydrazone 12 was then attached to nylon as shown in Scheme 7.

Scheme 7.

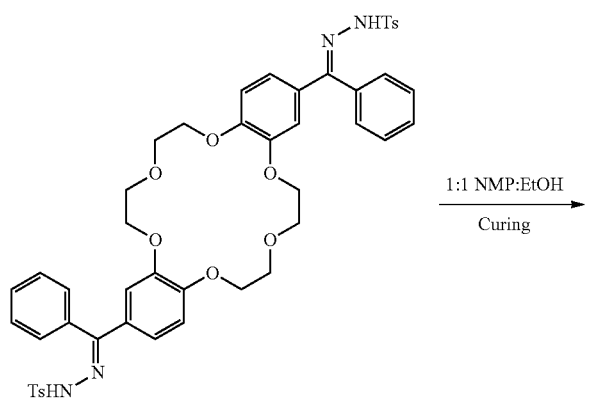

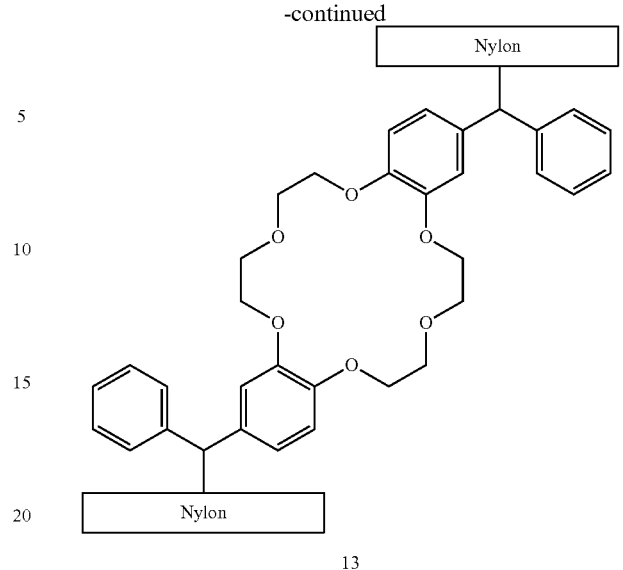

A 1 wt. % or 3 wt. % coating solution containing hydrazone 12 (0.41 g or 1.24 g) and NaOH (6 mmol, added as a 50% aqueous solution) in N-methyl-2-pyrrolidone (21 mL) and ethanol (21 mL) was prepared. On a benchtop dip coater using an 8 mils gap height, 4.5" by 10" strips of nylon were coated with the 1 wt. % or 3 wt. % coating solution. The coated nylon was cured in an oven at 85° C. for 2 hours. The initial uptake percentage was measured and then the coated nylon was cleaned by soaking the coated nylon in 3% HCl for 1 hour followed by soaking the coated nylon in deionized water for 1 hour. The coated nylon was then trickle washed with deionized water for 10 minutes and dried in an oven at 85° C. for 2 hours. The uptake percentage after cleaning and critical weight surface tension (CWST) of the coated nylon were measured. The results are set forth in Table 1.

TABLE 1

Crown Ether Coated Nylon Results

| Coating Solution | Initial Coating Uptake | Clean Coating Uptake | CWST (Dynes/cm$^2$) |
|---|---|---|---|
| Trial 1 (1 wt.%) | 6.7% | 2.8% | 73 |
| Trial 2 (1 wt.%) | 5.6% | 2.6% | 73 |
| Trial 3 (3 wt.%) | 14.3% | 8.4% | 65 |
| Trial 4 (3 wt.%) | 17.3% | 10.7% | 63 |

As is apparent from the results set forth in Table 1, the more concentrated hydrazone solution provided better crown ether uptake in the coated nylon. In addition, Table 1 shows that as the uptake increased, the critical weight surface tension (CWST) of the coated nylon decreased.

Example 7

This example demonstrates the metal removal efficiency of a material of formula (V), described herein.

Metal removal efficiency (MRE) testing was performed using a punched 47 mm coated material of Trial 4 of Example 6, which has been cleaned with a 5% HCl solution and deionized water. A 20-30 mL or 30-40 mL solution of propylene glycol methyl ether acetate (i.e., OK73 fluid) containing 1 ppb of each metal impurity (i.e., lithium, magnesium, aluminum, potassium, calcium, titanium, vanadium, chromium, manganese, iron, cobalt, nickel, copper, zinc, molybdenum, cadmium, tin, barium, tungsten, and lead) were passed through the disc and the resulting metal ion concentrations were measured by inductively coupled plasma-mass spectrometry (ICP-MS). The metal removal efficiency (i.e., the percent concentration removed) was calculated and the results for the 20-30 mL trial (left) or 30-40 mL (right) are plotted in the FIGURE.

As is apparent from the results set forth in the FIGURE, the nylon coated material of Trial 4 of Example 6 removed greater than 50% of magnesium, aluminum, potassium, calcium, manganese, iron, and barium, while selectively allowing ions such as lithium and sodium to pass through. In addition, the nylon coated material of Trial 4 of Example 6 was particularly effective at removing magnesium and barium, exhibiting greater than 90% MRE in both instances.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A material comprising (i) a crown ether of formula (I):

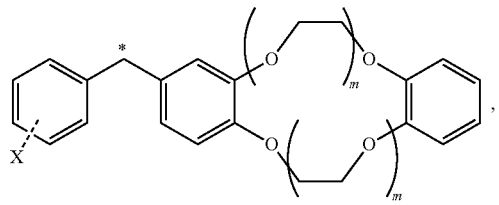

(ii) a crown ether of formula (II):

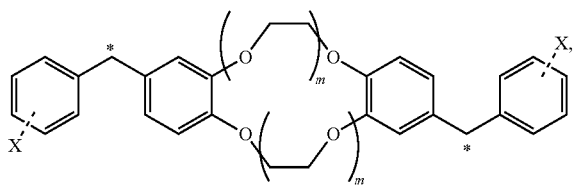

and/or (iii) a crown ether of formula (III):

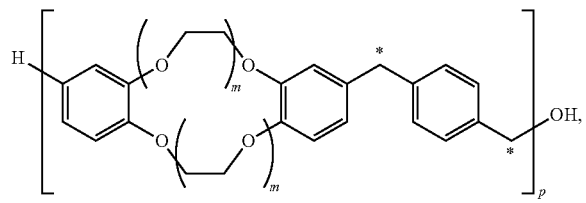

or a salt thereof, wherein each m independently is an integer from 1 to 8, p is an integer from 1 to 1000, each " ⁓ " designates an optionally present bond, each X is an optionally present substituent, each * independently represents —H, =O, or a bond to a remainder of the material, provided that at least one * is a bond to the remainder of the material, and wherein the remainder of the material is bound via a sp3-sp3 carbon-carbon bond.

2. The material of claim 1, wherein the material comprises a crown ether of formula (I):

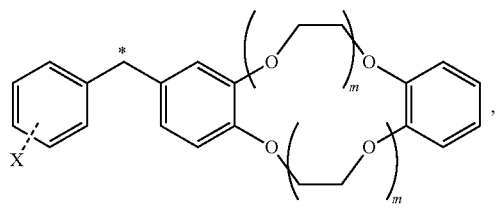

or a salt thereof, wherein each m independently is an integer from 1 to 8, each " ⁓ " designates an optionally present bond, each X is an optionally present substituent, and * represents a bond to a remainder of the material, wherein the remainder of the material is bound via a sp3-sp3 carbon-carbon bond.

3. The material of claim 1, wherein the material comprises a crown ether of formula (II):

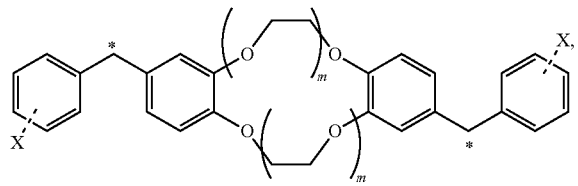

or a salt thereof, wherein each m independently is an integer from 1 to 8, each "⁓" designates an optionally present bond, each X is an optionally present substituent, each * independently represents —H, =O, or a bond to a remainder of the material, provided that at least one * is a bond to the remainder of the material, and wherein the remainder of the material is bound via a sp3-sp3 carbon-carbon bond.

4. The material of claim 1, wherein the material comprises a crown ether of formula (III):

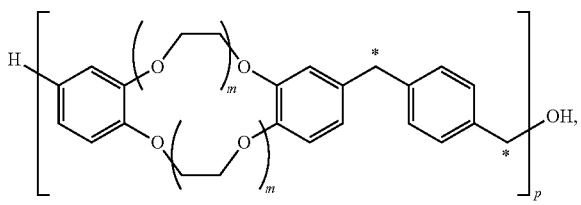

or a salt thereof, wherein each m independently is an integer from 1 to 8, p is an integer from 1 to 1000, and each * independently represents —H, =O, or a bond to a remainder of the material, provided that at least one * is a bond to the remainder of the material, and wherein the remainder of the material is bound via a sp3-sp3 carbon-carbon bond.

5. The material of claim 1, wherein each m independently is an integer from 1 to 4.

6. The material of claim 1, wherein each m independently is an integer selected from 1 or 2.

7. The material of claim 1, wherein each m is 2.

8. A material of formula (IV):

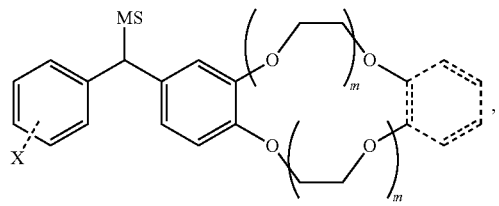

formula (V):

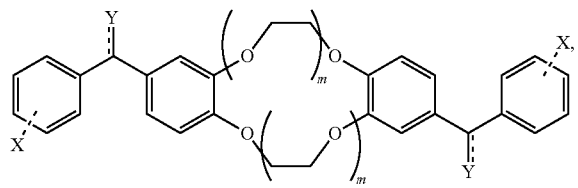

or formula (VT):

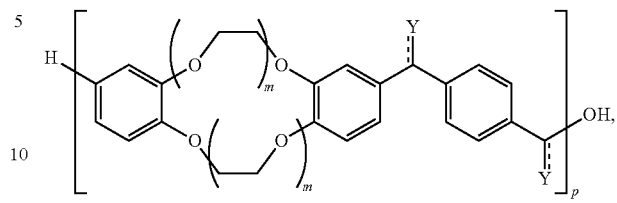

or a salt thereof, wherein each m independently is an integer from 1 to 8, p is an integer from 1 to 1000, each "⁓" designates an optionally present bond and/or structure, each X is an optionally present substituent, each Y is hydrogen, oxygen, or MS, provided that at least one Y is MS, and each MS independently is a macromolecular support selected from a membrane, a fibrous media, a polymeric coating or material, a metal organic framework, a monolith support, a bead, a filter, or a resin, and wherein MS is bound via an sp3-sp3 carbon-carbon bond.

9. The material of claim 8, wherein the material is of formula (IV):

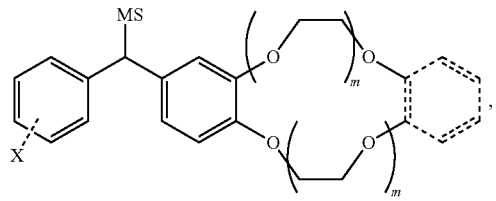

or a salt thereof, wherein each m independently is an integer from 1 to 8, each "⁓" designates an optionally present bond and/or structure, each X is an optionally present substituent, and MS is a macromolecular support selected from a membrane, a fibrous media, a polymeric coating or material, a metal organic framework, a monolith support, a bead, a filter, or a resin, and wherein MS is bound via an sp3-sp3 carbon-carbon bond.

10. The material of claim 8, wherein the material is of formula (V):

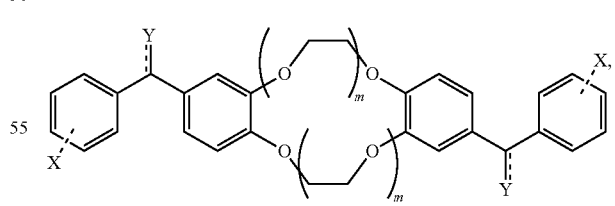

or a salt thereof, wherein each m independently is an integer from 1 to 8, each "⁓" designates an optionally present bond, each X is an optionally present substituent, each Y is hydrogen, oxygen, or MS, provided that at least one Y is MS, and each MS independently is a macromolecular support selected from a membrane, a fibrous media, a polymeric coating or material, a metal organic framework, a monolith support, a bead, a filter, or a resin, and wherein MS is bound via an sp3-sp3 carbon-carbon bond.

11. The material of claim 8, wherein the material is of formula (VI):

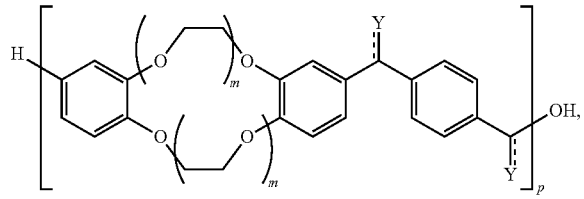

or a salt thereof, wherein each m independently is an integer from 1 to 8, p is an integer from 1 to 1000, each " " designates an optionally present bond, each Y is hydrogen, oxygen, or MS, provided that at least one Y is MS, and each MS independently is a macromolecular support selected from a membrane, a fibrous media, a polymeric coating or material, a metal organic framework, a monolith support, a bead, a filter, or a resin, and wherein MS is bound via an sp3-sp3 carbon-carbon bond.

12. The material of claim 8, wherein each m independently is an integer from 1 to 4.

13. The material of claim 8, wherein each m independently is an integer selected from 1 or 2.

14. The material of claim 8, wherein each m is 2.

15. The material of claim 8, wherein the macromolecular support comprises gelatin, alginate, starch, polyethylene, polypropylene, nylon, polyvinylidene fluoride, polyethylene oxide, polypropylene oxide, polyethylene/polypropylene oxide, poly acrylonitrile, poly(meth)acrylate, poly(meth) acrylamide, polyamide, polyimide, polyester, cellulose, polystyrene, or a combination thereof.

16. A method of making a material of claim 8, the method comprising:
(i) reacting a hydrazide or hydrazine with a crown ether of formula (VII):

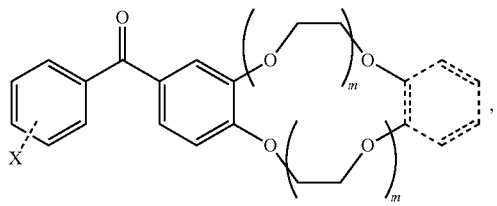

formula (VIII):

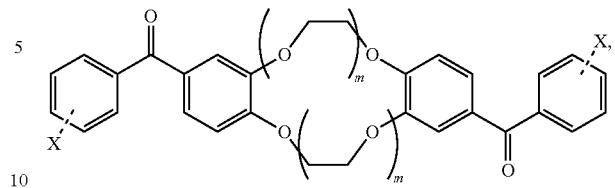

or
formula (IX):

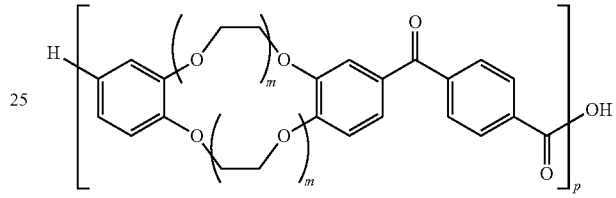

to form a hydrazone-containing compound, and
(ii) reacting the hydrazone-containing compound with a macromolecular support selected from a membrane, a fibrous media, a polymeric coating or material, a metal organic framework, a monolith support, a bead, a filter, or a resin to form at least one C—C bond.

17. The method of claim 16, wherein the hydrazide or hydrazide is p-toluenesulfonyl hydrazide.

18. A method of removing one or more metal ions from a solution comprising passing the solution through the material of claim 1, or a salt thereof.

19. The method of claim 18, wherein the solution is an aqueous solution.

20. The method of claim 18, wherein the method removes at least 50% of one or more metal ions selected from sodium, magnesium, aluminum, potassium, calcium, titanium, vanadium, chromium, manganese, iron, cobalt, nickel, copper, zinc, molybdenum, cadmium, tin, barium, tungsten, lead, or a combination thereof.

* * * * *